(12) United States Patent
Schürmann-Mader et al.

(10) Patent No.: US 7,678,565 B2
(45) Date of Patent: Mar. 16, 2010

(54) FLOW CELL ARRAY AND THE UTILIZATION THEREOF FOR MULTIANALYTE DETERMINATION

(75) Inventors: Eveline Schürmann-Mader, Zeihen (CH); Andreas Peter Abel, Basel (CH); Martin Andreas Bopp, Basel (CH); Gert Ludwig Duveneck, Bad Krozingen (DE); Markus Ehrat, Magden (CH); Gerhard Matthias Kresbach, Staufen (DE); Michael Pawlak, Laufenburg (DE); Nania Graciela Schärer-Hernández, Gelterkinden (CH); Eginhard Schick, Rheinfelden (DE)

(73) Assignee: Bayer Technology Services GmbH, Leverkusen (DE)

( * ) Notice: Subject to any disclaimer, the term of this patent is extended or adjusted under 35 U.S.C. 154(b) by 145 days.

(21) Appl. No.: 12/071,526

(22) Filed: Feb. 21, 2008

(65) Prior Publication Data

US 2008/0299008 A1 Dec. 4, 2008

Related U.S. Application Data

(63) Continuation of application No. 10/168,001, filed as application No. PCT/EP00/12668 on Dec. 13, 2000, now Pat. No. 7,358,079.

(30) Foreign Application Priority Data

Dec. 17, 1999 (CH) .................................... 2316/99
Mar. 21, 2000 (CH) .................................... 0543/00

(51) Int. Cl.
*C12M 1/34* (2006.01)
*C12M 3/00* (2006.01)

(52) U.S. Cl. ................ 435/287.1; 422/82.05; 422/68.1; 422/82.11; 435/7.1; 435/283.1; 435/287.2; 435/288.4; 436/518; 436/524

(58) Field of Classification Search ........................ None
See application file for complete search history.

(56) References Cited

U.S. PATENT DOCUMENTS 4,649,280 A 3/1987 Holland et al.

(Continued)

FOREIGN PATENT DOCUMENTS

WO 94/27137 11/1994

(Continued)

*Primary Examiner*—Melanie Yu
(74) *Attorney, Agent, or Firm*—Wenderoth, Lind & Ponack, L.L.P.

(57) ABSTRACT

A one- or two-dimensional arrangement of flow cells is provided, as part of an array of sample compartments, with at least one inlet and outlet for each sample compartment, formed by a base plate and a body, with an arrangement of spatial recesses corresponding to the (geometrical) arrangement of the sample compartments, combined with the base plate. The arrangement allows for supplying to or removing from the sample compartments, which can be arranged at a high quantity on a small base area, even very small amounts of samples or reagents. An arrangement of one or more sample compartments includes a base plate and a body combined with the base plate in such a way that one or more recesses for generation of one or more flow cells fluidically sealed against one another, each with at least one inlet and one outlet, are formed between the base plate and the body, wherein at least one outlet of each flow cell is joined with a reservoir fluidically connected with the flow cell, the reservoir being operable to receive liquid exiting the flow cell, besides methods for its manufacturing and their use.

57 Claims, 5 Drawing Sheets

U.S. PATENT DOCUMENTS

| | | |
|---|---|---|
| 4,978,503 A | 12/1990 | Shanks et al. |
| 5,006,716 A | 4/1991 | Hall |
| 5,019,351 A | 5/1991 | Schulz |
| 5,447,440 A | 9/1995 | Davis et al. |
| 5,478,755 A | 12/1995 | Attridge et al. |
| 5,747,274 A | 5/1998 | Jackowski |
| 5,822,472 A | 10/1998 | Danielzik et al. |
| 5,841,143 A | 11/1998 | Tuma et al. |
| 6,192,168 B1 | 2/2001 | Feldstein et al. |
| 6,242,267 B1 | 6/2001 | Herron et al. |
| 6,284,113 B1 | 9/2001 | Bjornson et al. |
| 6,480,639 B2 | 11/2002 | Hashimoto et al. |
| 6,787,368 B1 | 9/2004 | Wong et al. |

FOREIGN PATENT DOCUMENTS

| | | |
|---|---|---|
| WO | 95/33197 | 12/1995 |
| WO | 95/33198 | 12/1995 |
| WO | 96/35940 | 11/1996 |
| WO | 97/01087 | 1/1997 |
| WO | 97/35203 | 9/1997 |
| WO | 98/22799 | 5/1998 |
| WO | 98/41863 | 9/1998 |
| WO | 99/15876 | 4/1999 |

FLOW CELL ARRAY AND THE UTILIZATION THEREOF FOR MULTIANALYTE DETERMINATION

This application is a continuation of U.S. patent application Ser. No. 10/168,001, filed Jun. 17, 2002, now U.S. Pat. No. 7,358,079, which is the National Stage of International Application No. PCT/EP00/12668, filed Dec. 13, 2000.

The invention is related to a one- or two-dimensional arrangement of flow cells, as part of an array of sample compartments, with at least one inlet and outlet for each sample compartment, formed by a base plate and a body, with an arrangement of spatial recesses corresponding to the (geometrical) arrangement of the sample compartments, combined with the base plate. The arrangement allows for supplying to or removing from the sample compartments, which can be arranged at a high quantity on a small base area, even very small amounts of samples or reagents. For each sample compartment at least one reservoir for receiving liquids to be removed from the respective sample compartment is integrated in the arrangement, the peripheral manifold of liquid supply and removal means can be simplified significantly in comparison to conventional technical solutions.

For the determination of a single analyte in a sample, especially for diagnostics, numerous arrangements have become known, wherein the transport of samples or reagents is performed using capillary forces. Thus the use of pumps for fluidic transport can often be avoided. In U.S. Pat. No. 5,019,351 a special embodiment of such a device is described, wherein a reaction capillary with an inlet end and an outlet end is arranged between a base plate and a cover plate, the inlet end being fluidically connected with a region dedicated for receiving a sample and mixing the sample with reagents, and wherein the reaction capillary is divided into an upstrem region and a downstream region, with increasing thickness of the reaction capillary from the upstream region towards the downstream region. With this arrangement constant, reproducible flow conditions shall be achieved within the reaction capillary. Additionally, embodiments are described in that patent disclosure, wherein the outlet end of the reaction capillary is connected with a region for collecting exiting liquid. Thereby, all components of the structure, except for the inlet region, are provided in a continuous channel or capillary system, respectively, between the common base plate and a common cover plate. The essential technical background of the patent disclosure is based on liquid transport by the capillary effect.

However, especially because of the necessary large space requirements, such an arrangement of capillary-type flow cells is hardly suited for an application in combination with a multitude of measurement areas, for the determination of different analytes or the analysis of different samples, on a common support. Accordingly, there are not any hints towards array-type arrangements of several flow cells of this type in U.S. Pat. No. 5,019,351. Additionally, a removal of liquid having entered the collection region is not possible.

For the determination of a multitude of analytes, currently mainly such methods are used, wherein the determination of different analytes is performed in discrete sample compartments or "wells" of so-called microtiter plates. The most common are plates with a pitch (geometrical arrangements in rows and columns) of 8×12 wells on a footprint of typically about 8 cm×12 cm (see, for example, Corning Costar catalogue No. 3370, 1999), wherein a volume of some hundred microliters is required for filling a single well. It would be desirable for many applications, however, to reduce the sample volume considerably, not only for a reduction of necessary amounts of samples and reagents, which might be available only at small amounts, but especially for a reduction of the diffusion pathways and thus of the assay times, for assays wherein biological or biochemical or synthetic recognition elements for the recognition of one or more analytes in a sample are immobilized on the inner wall of a sample compartment.

In case of open sample compartments arranged in an array, derived from the classical microtiter plate, a well-known technical solution for a reduction of the volumes of the individual sample compartments was provided by arranging a larger number of wells on the same base area (foot print), for example 384 (see, for example, Corning Costar catalogue No. 3702, 1999) or 1536 instead of classically 96 wells. This approach has the advantage that the instruments and laboratory robots, established as the industrial standard, can be further used at least for a part of the necessary steps of sample manipulation, such as sample supply and removal. Other known technical solutions were provided by abandoning the classical plate foot print and adapting the size of the individual wells to the sample volumes required for a certain application, exclusively. Such arrangements became known under the name "nanotiter plates", the volumes of the individual sample compartments partially being only some nanoliters. However, this technical solution requires the abandonment of the currently wide-spread laboratory robots designed for the classical microtiter plate standard.

Along with the reduction of the size of the individual, open sample compartments and/or with the reduction of the thickness of the liquid layer on the base surface, desired for a reduction of the diffusion pathways, however, the increasing effect of liquid evaporation during the time of an assay becomes a more and more severe problem that has to be taken care of.

Said problem of evaporation can be avoided by using sample compartments that are closed, except for openings for sample inlet and outlet.

Such through-flow cells, operable for receiving a liquid sample and or reagents in a single flush or continuously, are known for the case of a single measurement area in contact with a sample compartment.

In U.S. Pat. No. 5,747,274, measurement arrangements and methods for the early recognition of a cardiac infarction, upon determination of several from at least three infarction markers, are described, wherein the determination of these markers can be performed in individual sample compartments or in a common sample compartment, a single (common) sample compartment being provided, according to the disclosure for the latter case, as a continuous flow channel, one demarcation of which being formed, for example, by a membrane, whereon antibodies for the three different markers are immobilized. However, there are no hints for an arrangement of several sample compartments or flow channels of this type on a common support. Additionally, there is no geometrical information concerning the size of the measurement areas.

Optical methods, for example based on the determination of the change of an absorbance or of a luminescence, have been developed for analyte determination in one or more samples to an increasing extent in the past, as such methods can be performed without contact and without significant effect on the sample itself. The classical measurement methods, such as absorption or fluorescence measurements, are generally based on the direct illumination of a sample volume in a sample compartment or of a measurement area on the inner wall of the compartment of a liquid sample. As a disadvantage of these configurations, in general a significant part of the surroundings, besides the excitation volume or excitation area where a signal for analyte determination shall be generated, is illuminated by excitation light, which can lead to disadvantageous generation of disturbing background signals.

For achieving lower detection limits, numerous measurement arrangements have been developed, wherein the determination of an analyte is based on its interaction with the evanescent field, which is associated with light guiding in an optical waveguide, wherein biochemical or biological recognition elements for the specific recognition and binding of the analyte molecules are immobilized on the surface of the waveguide. When a light wave is couples into an optical waveguide surrounded by optically rarer media, i.e. media of lower refractive index, the light wave is guided by total reflection at the interfaces of the waveguiding layer. In that arrangement, a fraction of the electromagnetic energy penetrates the media of lower refractive index. This portion is termed the evanescent (=decaying) field. The strength of the evanescent field depends to a very great extent on the thickness of the waveguiding layer itself and on the ratio of the refractive indices of the waveguiding layer and of the media surrounding it. In the case of thin waveguides, i.e. layer thicknesses that are the same as or smaller than the wavelength of the light to be guided, discrete modes of the guided light can be distinguished. As an advantage of such methods, the interaction with the analyte is limited to the penetration depth of the evanescent field into the adjacent medium, being of the order of some hundred nanometers, and interfering signals from the depth of the (bulk) medium can be mainly avoided. The first proposed measurement arrangements of this type were based on highly multi-modal, self-supporting single-layer waveguides, such as fibers or plates of transparent plastics or glass, with thicknesses from some hundred micrometers up to several millimeters.

In U.S. Pat. No. 4,978,503, a measurement arrangement is disclosed, wherein a liquid sample is drawn into a cavity by capillary forces, wherein an optically transparent side wall is provided as a self-supporting multimode waveguide, wherein at least on a part of the surface of that side wall ("patch"), facing the cavity, a biochemical recognition element for the recognition and binding of an analyte from a sample is immobilized. As a disadvantage of this arrangement, an exchange of the liquid drawn into the capillary is not provided for, such an exchange being for example desirable for a multi-step assay.

In WO 94/27137, measurement arrangements are disclosed, wherein "patches" with different recognition elements, for the determination of different analytes, are immobilized on a self-supporting optical substrate waveguide (single-layer waveguide), excitation light being incoupled at the distal surfaces ("front face" or "distal end" coupling), wherein laterally selective immobilization is performed using photo-activatable cross-linkers. According to the disclosure, several patches can be arranged row-wise in common, parallel flow channels or sample compartments, wherein the parallel flow channels or sample compartments extend over the whole length of the range on the waveguide used as a sensor, in order to avoid an impairment of light guiding in the waveguide. However, there are no hints to a two-dimensional integration of multiple patches and sample compartments. In a similar arrangement disclosed in WO 97/35203, several embodiments of an arrangement are described, wherein different recognition elements for the determination of different analytes are immobilized in separate, parallel flow channels or sample compartments for the sample and for calibration solutions of low and, optionally in addition, of high analyte concentration. Again, no hint to two-dimensional arrangements is given.

For an improvement of the sensitivity and simultaneously for an easier manufacturing in mass production, planar thin-film waveguides have been proposed. In the simplest case, a planar thin-film waveguide consists of a three-layer system: support material (substrate), waveguiding layer, superstrate (respectively the sample to be analyzed), wherein the waveguiding layer has the highest refractive index. Additional intermediate layers can further improve the action of the planar waveguide.

Several methods for the incoupling of excitation light into a planar waveguide are known. The methods used earliest were based on front face coupling or prism coupling, wherein generally a liquid is introduced between the prism and the waveguide, in order to reduce reflections due to air gaps. These two methods are mainly suited with respect to waveguides of relatively large layer thickness, i.e. especially self-supporting waveguides, and with respect to waveguides with a refractive index significantly below 2. For incoupling of excitation light into very thin waveguiding layers of high refractive index, however, the use of coupling gratings is a significantly more elegant method.

Different methods of analyte determination in the evanescent field of lightwaves guided in optical film waveguides can be distinguished. Based on the applied measurement principle, for example, it can be distinguished between fluorescence, or more general luminescence methods, on one side and refractive methods on the other side. In this context methods for generation of surface plasmon resonance in a thin metal layer on a dielectric layer of lower refractive index can be included in the group of refractive methods, if the resonance angle of the launched excitation light for generation of the surface plasmon resonance is taken as the quantity to be measured. Surface plasmon resonance can also be used for the amplification of a luminescence or the improvement of the signal-to-background ratios in a luminescence measurement. The conditions for generation of a surface plasmon resonance and the combination with luminescence measurements, as well as with waveguiding structures, are described in the literature, for example in U.S. Pat. Nos. 5,478,755, 5,841, 143, 5,006,716, and 4,649,280.

In this application, the term "luminescence" means the spontaneous emission of photons in the range from ultraviolet to infrared, after optical or other than optical excitation, such as electrical or chemical or biochemical or thermal excitation. For example, chemiluminescence, bioluminescence, electroluminescence, and especially fluorescence and phosphorescence are included under the term "luminescence".

In case of the refractive measurement methods, the change of the effective refractive index resulting from molecular adsorption to or desorption from the waveguide is used for analyte detection. This change of the effective refractive index is determined, in case of grating coupler sensors, from changes of the coupling angle for the in- or out-coupling of light into or out of the grating coupler sensor, in case of interferometric sensors from changes of the phase difference between measurement light guided in a sensing branch and a referencing branch of the interferometer.

The aforesaid refractive methods have the advantage that they can be applied without using additional marker molecules, so-called molecular labels. The disadvantage of these label-free methods, however, is that the achievable detection limits are limited to pico- to nanomolar concentration ranges, dependent on the molecular weight of the analyte, due to lower selectivity of the measurement principle, which is not sufficient for many applications of modern trace analysis, for example for diagnostic applications.

For achieving lower detection limits, luminescence-based methods appear as more adequate, because of higher selectivity of signal generation. In this arrangement, luminescence excitation is limited to the penetration depth of the evanescent field into the medium of lower refractive index, i.e to the immediate proximity of the waveguiding area, with a penetration depth of the order of some hundred nanometers into the medium. This principle is called evanescent luminescence excitation.

By means of highly refractive thin-film waveguides, based on an only some hundred nanometers thin waveguiding film on a transparent support material, the sensitivity could be increased considerably during the last years. In WO 95/33197, for example, a method is described, wherein the excitation light is coupled into the waveguiding film by a relief grating as a diffractive optical element. The isotropically emitted luminescence from substances capable of luminescence, that are located within the penetration depth of the evanescent field, is measured by adequate measurement devices, such as photodiodes, photomultipliers or CCD cameras. The portion of evanescently excited radiation, that has back-coupled into the waveguide, can also be out-coupled by a diffractive optical element, like a grating, and be measured. This method is described, for example, in WO 95/33198.

For performing, simultaneously or sequentially, exclusively luminescence-based, multiple measurements with essentially monomodal, planar anorganic waveguides, for example in the specification WO 96/35940, arrangements (arrays) have been proposed, wherein at least two discrete waveguiding areas are provided on one sensor platform, such that the excitation light guided in one waveguiding area is separated from other waveguiding areas.

In the spirit of this invention, spatially separated measurement areas (d) (according to FIG. 4) shall be defined by the area that is occupied by biological or biochemical or synthetic recognition elements immobilized thereon, for recognition of one or multiple analytes in a liquid sample. These areas can have any geometry, for example the form of dots, circles, rectangles, triangles, ellipses or lines.

In WO 98/22799, arrangements of sample compartments for measurement configurations for the determination of luminescence excited in the evanescent field of a planar waveguide are proposed, wherein the gratings used for incoupling of the excitation light are covered by the material forming the side walls of the sample compartments. Thus, any change of the incoupling conditions can be avoided. This is, however, associated with very high requirements on the transparency, freedom of fluorescence and a refractive index of the side wall material as low as possible, which combination of requirements can hardly be satisfied simultaneously.

As a disadvantage, all devices described in the known technical state of the art do either not allow for an exchange of sample or reagent liquids or require relatively complex arrangements for such an exchange, namely the interfacing to fluidically sealing supplies and tube connections, for the supply and removal of liquid samples and reagents, especially impeding an automated operation and exchange of combinations of base plates, used as sensor platforms, with bodies placed thereon, for providing flow cells, for single use operation, or requiring complex technical solutions.

Therefore, there is a need for a simple arrangement of flow cells, especially in the form of one- or two-dimensional arrays, wherein the supply of sample solutions and reagents and the removal of exiting sample and reagent fluids can be simplified significantly, without impairing the measurement accuracy in a negative way.

Surprisingly, it now has been found, that a multitude of sample compartments can be provided on a small base area, without the requirement of a complex system of peripheral supply and removal lines for an automated supply and removal of samples and reagents, thanks to the design of sample compartments according to the invention, the sample compartments being each provided with a reservoir, for example in form of a recess in an exterior sample compartment wall, for receiving liquids exiting the sample compartments. Simultaneously, the volume capacities of the individual sample compartments can be kept low, even when relatively large base areas of the sample compartments on a base plate are required for generation of a sufficiently high measurement signal, because the sample compartments are closed except for inlet and outlet openings for sample and reagent supply and removal, and because the height of a sample compartment, i.e. the distance between a base plate and the opposite demarcation of a recess in a body combined with the base plate, can be kept very small, i.e. even below 100 µm.

Due to this arrangement, even very low sample volumes can be administered and kept constant. Due to the possible small volumes, the flow cells provided by the arrangement according to the invention can be cleaned very efficiently by displacement washing. If biological or biochemical or synthetic recognition elements for the determination of an analyte are immobilized on the base plate, as described below for some embodiments of an arrangement according to the invention, the end-point of diffusion-controlled analyte binding is reached fast, due to only short diffusion pathways towards the analyzing surface, which is another advantage. It is also favorable, that a signal caused by the analyte binding is essentially independent of the total volume of a supplied sample, as long as at least the flow cell, as part of an arrangement according to the invention, is filled completely. The flow cells being closed except for inlets and outlets, an evaporation of liquid can mainly be avoided, allowing for operation of the arrangement also at temperatures significantly above room temperature. In summary, the present invention thus provides significant advantages in comparison to the known state of the art.

The subject of the invention is an arrangement of one or more sample compartments in a one- or two-dimensional array, comprising a base plate and a body combined with the base plate in such a way, that an array of recesses for generation of an array of flow cells fluidically sealed against one another, each with at least one inlet and one outlet, are formed between the base plate and the body, wherein at least one outlet of each flow cell is joined with a reservoir fluidically connected with the flow cell, the reservoir being operable to receive liquid exiting the flow cell.

Thereby, the reservoir for receiving liquid exiting the flow cell is formed as a recess in the exterior wall of the body combined with the base plate.

The arrangement according to the invention allows for supplying simultaneously, locally addressed, numerous different sample and reagent solutions to different sample compartments, without the necessity of removing liquids that may have been supplied in advance. This does not require fixed tubing connections, but can be performed, for example using the squirt of a dispenser, which can be directed to the inlet of a flow cell of the arrangement according to the invention. The reservoirs for receiving liquids exiting from the flow cells being integrated in the arrangement, exit tubes and their connections, which would be required otherwise, are not needed.

Thus, a multitude of flow cells for analysis of different samples can be integrated on a minimum base area.

For the simultaneous supply of samples or reagents to a multitude of sample compartments, multi-channel pipettors for manual or automated reagent administration can be used, wherein the individual pipettes are arranged in one- or two-dimensional arrays, provided that the inlets of the arrangement of sample compartments according to the invention are arranged in the same pitch (geometrical arrangement in rows and/or columns). Preferably, therefore, the pitch of the arrangement corresponds to the pitch of the wells of a standard microtiter plate. Thereby, an arrangement of 8×12 wells at a (center-to-center) distance of about 9 mm is established as the industrial standard. Smaller arrays with, for example, 3, 6, 12, 24 and 48 wells, arranged at the same distance, are compatible with this standard. Several arrangements of sample compartments, according to the invention, provided as smaller arrays of flow cells, can also be combined in such a way, that the individual inlets of the flow cells are located at a whole-numbered multiple of the distance of about 9 mm.

Recently, also plates with 384 and 1536 wells, as a whole-numbered multiple of 96 wells on the same foot print at a correspondingly reduced well-to-well distance, are used, which shall also be called standard microtiter plates. By adaptation of the pitch of the sample compartments in the arrangement according to the invention, including the in- and outlets of each flow cells, to these standards, numerous commercially established and available laboratory pipettors and robots can be used for sample supply.

It is preferred that the exterior dimensions of the arrangement according to the invention correspond to the foot print of these standard microtiter plates.

Whereas the sample supply is performed in the center of the open sample compartments in case of commercially available microtiter plates, it is advantageous for the arrangement according to the invention, due to physical reasons, if the in- and outlets and the corresponding inlet and outlet openings are arranged at the border of the corresponding flow cells, for example at corner points opposite to each other, preferably, however, at the diagonally opposite corner points, as it is shown in one of the examples of break-down-to-praxis. Therefore, the position of the whole array, of e.g. 8×12 cells in case of an arrangement of 96 flow cells, is preferably slightly displaced from the position of the cells of a classical microtiter plate with respect to its foot print, thus allowing to address the inlets and/or reservoirs using standard laboratory robots, without the requirement for re-programming. This is achieved with a displacement of 4.5 mm with respect to the two main borders (axes) in case of the 96-well pitch, and, correspondingly, of 2.25 mm, in case of the 384-well pitch, and of 1.125 mm, in case of the 1536-well pitch. Due to technical reasons (available wall thickness of the arrangement) a displacement of 2.25 mm is preferred, such that the arrangement according to the invention can be addressed by robots provided for the 384-standard, without a modification of their programming.

A further subject of the invention is an arrangement with, for example, 2 to 8 sample compartments in a column, with the properties as described above, or, for example, 2 to 12 sample compartments in a row, which themselves are combined with a carrier ("meta-carrier") with the dimensions of standard microtiter plates in such a way, that the pitch (geometrical arrangement in rows and/or columns) of the inlets of the flow cells does correspond to the pitch (geometrical arrangement) of the wells of a standard microtiter plate.

The adjoining of the arrangement of sample compartments with the meta-carrier can, for example, be performed by glueing or by exact fitting without glueing, if it is intended for single-use, or, for example by latching or inserting, if it is intended for multiple use. The material of the meta-carrier can, for example, be selected from the group comprising formable, moldable or millable plastics, metals, silicates, such as glass, quartz or ceramics.

Several rows or columns of such sample compartments can also be combined with a single meta-carrier in such a way that the pitch (geometrical arrangement in rows and/or columns) of the inlets of the flow cells corresponds to the pitch (geometrical arrangement) of the wells of a standard microtiter plate, i.e., to a whole-numbered multiple of 9 mm (corresponding to a 96-well plate) or of 4.5 mm (corresponding to a 384-well plate, see above) or of 2.25 mm (corresponding to a 1536-well plate, see above).

Of course, the arrangement of sample compartments according to the invention can also be arranged in another pitch (geometry). Liquid exiting a flow cell, for example after sequential addition of different reagents, can be collected in the reservoir fluidically connected with the corresponding flow cell or also be removed by exhausting at the position of the inlet or of the reservoir.

There are several technical solutions for the generation of the spatial recesses between the base plate and the body combined therewith. In one possible arrangement, three-dimensional structures, with the pitch (geometrical arrangement in rows and/or columns) of the arrays of flow cells to be generated, are formed on the base plate. These structures on the base plate can, for example, form the walls or parts of the walls, such as sockets, between flow cells adjacent to each other, which flow cells are formed by combination of the base plate with an adequately formed body. For generation of the array of flow cells, that, for generation of the spatial recesses between the base plate and the body combined therewith, these recesses are formed in the base plate.

A characteristic for another embodiment is, that, for generation of the recesses between the base plate and the body combined therewith, recesses are formed in the body. For this embodiment, it is preferred that the base plate is essentially planar.

The body to be combined with the base plate for the generation of the array of flow cells can consist of a single workpiece. In another embodiment, the body combined with the base plate is formed from several parts, wherein the combined parts of the body preferably form an irreversibly combined unit.

It is preferred that the body combined with the base plate comprises auxiliary means facilitating the combination of the body and the base plate.

It is further preferred that the arrangement comprises a multitude, i.e., 2-2000, preferably 2-400, most preferably 2-100 flow cells.

Preferably, the pitch (geometrical arrangement in rows and/or columns) of the inlets of the flow cells corresponds to the pitch (geometrical arrangement) of the wells of a standard microtiter plate.

A characteristic for another embodiment of the arrangement is that it is closed by a covering top, such as a foil, membrane or cover plate.

The capacity of the flow cells can be varied within a large range upon variation of the size of the base areas and of the depth of the recesses, so that the inner volume of each flow cell is typically 0.1 µl-1000 µl, preferably 1 µl-20 µl. Thereby, the inner volumes of different flow cells can be similar or different.

If different sample or reagent solutions are filled sequentially into a flow cell, typically a multiple liquid volume of the cell volume is applied, in order to displace as completely as possible the liquid and components dissolved therein, which had been added before. Therefore, it is preferred that the capacity of the reservoir fluidically connected to the flow cell is larger, preferably at least 5 times larger than the inner volume of the flow cell.

It is preferred that the depth of the recesses between the base plate and the body combined with the base plate is 1-1000 µm, preferably 20-200 µm. The size of the recesses of an array can be uniform or diverse and the base areas can have any geometry, preferably rectangular or polygonal or also other geometry. The lateral dimensions of the base areas can be varied within a large range as well, wherein typically the base areas of the recesses between the base plate and the body combined with the base plate are 0.1 mm²-200 mm², preferably 1 mm²-100 mm². It is preferred, that the corners of the base areas are rounded. Rounded corners affect the flow profile in a favorable way and facilitate the removal of gas bubbles that might be formed, and respectively prevent their formation.

The materials for the baseplate, the body combined therewith, and the optional additional covering top have to satisfy the requirements of the actually intended application. Dependent on the specific application, these requirements are related to chemical and physical stability, for example upon exposure to acidic or basic media, salts, alcohols or detergents as parts of aqueous solutions, or to formamide, to stability upon temperature variations (e.g. between −30° C. and 100° C.), to thermal expansion coefficients of the base plate and of the body combined therewith as similar as possible, to optical properties (such as non-fluorescence, reflectivity), to mechanical workability, etc. It is preferred that the material of the body combined with the base plate is selected from the group formed by formable, moldable or millable plastics, metals, silicates, such as glass, quartz or ceramics. Also the material of the additional, contiguous covering top can be selected from the group formed by formable, moldable or millable plastics, metals, silicates, such as glass, quartz or ceramics. Concerning the base plate, it is also preferred that its material comprises materials from the group formed by formable, moldable or millable plastics, metals, silicates, such as glass, quartz or ceramics. Thereby, the aforementioned components (base plate, body combined therewith, covering top) can be composed of a uniform material or can comprise a mixture or a composition adjoined in layers or laterally of different materials, wherein the materials can substitute each other.

A characteristic for a preferred embodiment is that biological or biochemical or synthetic recognition elements for the determination of one or more analytes are immobilized on the base plate.

The simplest method of immobilization consists in physical adsorption, for example due to hydrophobic interaction between the recognition elements and the base plate. However, the extent of these interactions can be affected strongly by the composition of the medium and its physical-chemical properties, such as polarity and ionic strength. Especially in case of sequential addition of different reagents in a multi-step assay, the adhesion of the recognition elements on the surface, after only adsorptive immobilization, is often insufficient. In an advanced embodiment of the arrangement, the adhesion is improved by deposition of an adhesion-promoting layer (f) (according to FIG. 4) on the base plate for the immobilization of the biological or biochemical or synthetic recognition elements. It is preferred that the adhesion-promoting layer (f) has a thickness of less than 200 nm, preferably of less than 20 nm. For the generation of the adhesion-promoting layer, many materials can be used. Without any restriction, it is preferred that the adhesion-promoting layer (f) comprises chemical compounds from the groups of silanes, epoxides, "self-organized functionalized monolayers", functionalized polymers and polymer gels.

In case of the simultaneous determination of different analytes, preferably upon their binding to different, selective recognition elements, it is of advantage, if the registration of these binding events can be performed by detection of laterally resolved signals. A characteristic of an advanced embodiment of the arrangement according to the invention is that the biological or biochemical or synthetic recognition elements are immobilized in discrete (laterally separated) measurement areas (d). These discrete measurement areas can be formed by spatially selective deposition of the biological or biochemical or synthetic recognition elements on the base plate. Numerous methods can be used for the deposition. It is preferred without any restriction of generality that the biological or biochemical or synthetic recognition elements are deposited on the base plate by one or more methods from the group of methods comprising "ink jet spotting, mechanical spotting by means of pin, pen or capillary, "micro contact printing", fluidically contacting the measurement areas with the biological or biochemical or synthetic recognition elements upon their supply in parallel or crossed micro channels, upon exposure to pressure differences or to electric or electromagnetic potentials.

As the biological of biochemical or synthetic recognition elements, components from the groups formed by nucleic acids (DNA, RNA) or nucleic acid analogues (for example peptide nucleic acids PNA), antibodies, aptamers, membrane-bound and isolated receptors, their ligands, antigens for antibodies, cavities generated by chemical synthesis to host molecular imprints, and "histidin-tag components", are deposited. Also whole cells and cell fragments can be deposited as biological or biochemical or synthetic recognition elements.

The arrangement according to the invention is intended for numerous applications, wherein not only a single, but two or more analytes in a sample shall be determined. Therefore, it is preferred that arrays of two or more discrete measurement areas (d) each are arranged in the regions of the recesses between the base plate and the body combined with the base plate, in which measurement areas similar or different biological or biochemical or synthetic recognition elements are immobilized.

In general, the immobilized recognition elements are selected in such a way that they recognize and bind the analyte to be determined with a specificity as high as possible. Typically however, it must be expected that also a nonspecific adsorption of analyte molecules on the surface of the base plate occur especially if there are still empty sites between the recognition elements immobilized in the measurement areas. Therefore, it is preferred that compounds which are "chemically neutral" towards the analyte are deposited between the discrete measurement areas (d), in order to reduce nonspecific binding or adsorption. As "chemically neutral" compounds such components are meant, which do not show a recognition or binding of the analyte, such that no or only minimum nonspecific binding occurs. The choice of these compounds is dependent on the properties of the analyte. Without any restriction it is preferred that the "chemically neutral" compounds are selected from the groups comprising, for example, albumins, especially bovine and human serum albumin, herring sparm or also polyethylen glycols.

The arrangement according to the invention can be used for the determination of numerous different parameters (measurands), wherein the specific embodiment, especially of the baseplate, is dependent on the actually applied measurement method. One subject of the invention is an arrangement, wherein the base plate with the biological or biochemical or synthetic recognition elements immobilized thereon is operable for the determination of a change of optical, electrical, electrochemical or thermal parameters, or for the determination of radioactive radiation. It is preferred that the base plate with the biological or biochemical or synthetic recognition elements immobilized thereon is operable for the determination of a change of optical parameters, and that the base plate is transparent in at least one region of wavelengths in the visible or near-infrared spectral region. It is especially preferred that the base plate comprises a supporting substrate of glass or of a thermoplastic or moldable plastic, which is transparent in at least one region of wavelengths in the visible or near-infrared spectral region.

Within the optical detection methods, the methods based on analyte detection within the evanescent field of a waveguide are characterized by improved sensitivity and by restriction of the detection volume to the layer penetrated by the evanescent field, in proximity to the waveguide. Therefore, it is preferred that the base plate comprises an optical waveguide, which is continuous or partitioned into discrete areas. Thereby, especially preferred is an arrangement, wherein the optical waveguide is an optical film waveguide with a first optically transparent layer (a), facing the recesses, on a second optically transparent layer (b) with lower refractive index than layer (a) (according to FIG. 4). Thereby, the terminus "optical transparency" means (here and in the following) transparency at one or more excitation wavelengths in the visible or near-infrared spectral range.

The optically transparent layer (b) should be characterized by low absorption and fluorescence, in the ideal case free of absorption and fluorescence. Additionally, the surface roughness should be low, because the surface roughness of the layer (b) does affect, dependent on the deposition process to a more or less large extent, the surface roughness of an additional layer (a) of higher refractive index, when it is deposited on layer (a) as a waveguiding layer. An increased surface roughness at the boundary (interface) layers of layer (a) leads to increased scattering losses of the guided light, which, however, is undesired. These requirements are fulfilled by numerous materials. It is preferred that the material of the second optically transparent layer (b) comprises silicates, such as glass or quartz, or a transparent thermoplastic or moldable plastic, preferably of the group comprising polycarbonate, polyimide, or polymethylmethacrylate, or polystyrene.

For a given layer thickness of the optically transparent layer (a), the sensitivity of an arrangement according to the invention increases along with an increase of the difference between the refractive index of layer (a) and the refractive indices of the adjacent media, i.e., along with an increase of the refractive index of layer (a). It is preferred that the refractive index of the first optically transparent layer (a) is higher than 1.8.

Another important requirement on the properties of layer (a) is that the propagation losses of the light guided in layer (a) should be as low as possible. It is preferred that the first optically transparent layer (a) comprises $TiO_2$, $ZnO$, $Nb_2O_5$, $Ta_2O_5$, $HfO_2$, or $ZrO_2$, preferably $TiO_2$, $Ta_2O_5$ or $Nb_2O_5$. Combinations of several such materials can also be used.

For a given material of layer (a) and given refractive index, the sensitivity increases with decreasing layer thickness, up to a certain lower limiting value of the layer thickness. The lower limiting value is determined by the cut-off of light guiding, if the layer thickness falls below a threshold value determined by the wavelength of the light to be guided, and by an observable increase of the propagation losses in very thin layers, with further decrease of their thickness. It is preferred that the thickness of the first optically transparent layer (a) is between 40 and 300 nm, preferably between 100 and 200 nm.

If an autofluorescence of layer (b) cannot be excluded, especially if it comprises a plastic such as polycarbonate, or for reducing the effect of the surface roughness of layer (b) on the light guiding in layer (a), it can be advantageous, if an intermediate layer is deposited between layers (a) and (b). Therefore, it is characteristic for another embodiment of the arrangement according to the invention, that an additional optically transparent layer (b') (according to FIG. IV) with lower refractive index than and in contact with layer (a), and with a thickness of 5 nm-10 000 nm, preferably of 10 nm-1000 nm, is located between the optically transparent layers (a) and (b).

Many methods are known for the in-coupling of excitation light into an optical waveguide. In case of relatively thick waveguiding layers, up to self-supporting waveguides, the light can be focused into a front end (distal end) of the waveguide, using lenses of adequate numerical aperture, in such a way, that it is guided by internal total reflection. In case of waveguides with larger width of the front face than thickness, then preferably cylindrical lenses are used. Thereby, the lenses can be arranged remote from the waveguide or can also be directly connected to it. This method of front face coupling is less suited in case of lower thicknesses of the waveguiding layer. A more adequate method is then the coupling by prisms, which are preferably connected to the waveguide without any intermediate spacing or mediated by an index-matching fluid. It is also possible to supply the excitation light to the optical waveguide of the arrangement according to the invention by means of an optical fiber, or to couple light that has been in-coupled into another waveguide into the waveguide of said arrangement, upon bringing both waveguides in such a proximity to each other, that their evanescent fields overlap, thus enabling the energy transfer. Therefore, a part of the arrangement according to the invention is that the in-coupling of excitation light into the optically transparent layer (a), to the measurement areas (d), is performed using one or more optical in-coupling elements from the group comprising prism couplers, evanescent couplers comprising joined optical waveguides with overlapping evanescent fields, front face (distal end) couplers with focusing lenses arranged in front of a front face (distal end) of the waveguiding layer, and grating couplers.

It is preferred that the in-coupling of excitation light into the optically transparent layer (a), to the measurement areas (d), is performed using one or more grating structures (c) (according to FIG. 4), that are formed in the optically transparent layer (a).

A further part of the invention is, that the out-coupling of light guided in the optically transparent layer (a) is performed using grating structures (c') (according to FIG. 4), that are formed in the optically transparent layer (a).

Thereby, grating structures (c) and (c') formed in the optically transparent layer (a) can have the same or different periodicity and can be arranged in parallel or not in parallel to one another.

The arrangement can be provided in such a way that grating structures (c) and (c') can interchangeably be used as in-coupling and/or out-coupling gratings.

It is preferred that the grating structures (c) and optional additional grating structures (c') have a period of 200 nm-1000 nm and a grating modulation depth of 3 nm-100 nm, preferably of 10 nm-30 nm.

Thereby, it is preferred that the ratio of the modulation depth to the thickness of the first optically transparent layer (a) is equal or smaller than 0.2.

The grating structure can be provided in different forms (geometry). It is preferred that the grating structure (c) is a relief grating with any profile, such as rectangular, triangular or semi-circular profile, or a phase or volume grating with a periodic modulation of the refractive index in the essentially planar optically transparent layer (a).

A characteristic for an advanced embodiment of the arrangement is that a thin metal layer, preferably of gold or silver, optionally on an additional dielectric layer of lower refractive index than layer (a), for example of silica or magnesium fluoride, is deposited between the optically transparent layer (a) and the immobilized biological or biochemical recognition elements, wherein the thickness of the metal layer and the optional, additional intermediate layer is selected in such a way that a surface plasmon at the excitation wavelength and/or at the luminescence wavelength can be excited.

For one embodiment of the arrangement it is preferred that the grating structure (c) is a diffractive grating with a uniform period.

For specific applications however, for example for in-coupling simultaneously excitation light of different wavelengths, it can be of advantage if the grating structure (c) is a multi-diffractive grating.

Usually it is preferred that grating structures (c) and optional additional grating structures (c') are located within the region of the sample compartments.

If however, for example, very small sample volumes shall be applied on a very small base area, it can be advantageous if grating structures (c) and optional additional grating structures (c') are located outside the region of the sample compartments.

For applications, wherein a number as high as possible, of sample compartments within one sample compartment, shall be provided, and wherein simultaneously a propagation of the guided excitation light to adjacent sample compartments, in the direction of propagation of the guided excitation light, shall be prevented by means of its controlled outcoupling, it is preferred that the grating structures (c) are located within the region of the sample compartments, and that optional additional grating structures (c') are located outside of the sample compartment, within which the incoupling of the excitation light is performed.

Especially in case of sequential execution of measurements in different sample compartments, the gratings structures can be arranged in such a way that the excitation light is in-coupled by a grating structure (c) within one sample compartment, propagates through the sample compartment (guided in the waveguiding layer), and enters the waveguiding layer under an adjacent sample compartment, located in direction of propagation of the guided excitation light, where it is out-coupled by means of a grating structure (c') provided therein. After lateral displacement of the arrangement, the last-mentioned grating structure (c') can be used as in-coupling grating itself for a subsequent measurement.

Also additional embodiments of the arrangement according to the invention are provided, wherein grating structures (c) and optional additional grating structures (c') extend over the range of multiple or all sample compartments.

Multiple grating structures (c) and (c') can also be located within one sample compartment, for sequential measurements within a single sample compartment.

For most applications of the arrangement, it is preferred that the material of the body combined with the baseplate, in the incumbent surface area on the base plate, is optically transparent, both for the excitation radiation and for one or more optionally excited luminescence radiations, at least within the penetration depth of the evanescent field.

In an advanced embodiment, the material of the body combined with the base plate is provided in form of a two-layer system, the first layer of which, to be brought into contact with the surface of the base plate, being transparent both for the excitation radiation and optionally for one or more excited luminescence radiations, whereas the adjacent layer, being located more remote from the base plate, is absorbent in the spectral range of the excitation radiation and of the optionally excited luminescence radiations.

If an optical cross-talk of excitation light between adjacent sample compartments shall be minimized, it is advantageous to interrupt or minimize (as far as possible) the waveguiding upon contacting the waveguide in the intermediate regions between the sample compartments with an absorbent material. This is especially advantageous, if light in- and outcoupling by grating structures (c), respectively (c'), is performed within the sample compartments, or if a large-area grating structure extends over a multitude of sample compartments and a large area is illuminated with excitation light. It is characteristic for such an advanced embodiment, that the material of the layer in contact with the base plate is absorbent in the spectral range of the excitation radiation and of the optionally excited luminescence radiations.

It is of advantage if the material of the layer in contact with the base plate is self-adhesive and tightly sealing. Thereby, it is preferred that the material of the layer in contact with the base plate comprises a polysiloxane.

The arrangement according to the invention is operable to determine simultaneously a multitude of analytes in one sample. Therefore, it is advantageous if 5-1000, and preferably 10-400 measurement areas are located in one sample compartment.

For an advanced embodiment, it is preferred that optically or mechanically recognizable marks are provided on the base plate, in order to facilitate the adjustment in an optical system and/or to facilitate the combination of the base plate with the body comprising the recesses for the sample compartments.

A further subject of the invention is an analytical system for the determination of one or more analytes, comprising
an arrangement according to any of the aforementioned embodiments
means for the locally addressed supply of samples or reagents to the sample compartments of the arrangement, and at least one detector for the detection of a change of a parameter (measurand) due to the presence of the one or more analytes, which parameter (measurand) preferably is an optical, electrical, electrochemical or thermal parameter (measurand) or a signal from radioactive radiation.

A subject of the invention is also an analytical system for the determination of one or more luminescences comprising
an arrangement according to any of the aforementioned embodiments
means for the locally addressed supply of samples or reagents to the sample compartments of the arrangement
at least one excitation light source, and at least one detector for the detection of the light emanating from the at least one or more measurement areas (d) on the base plate.

Preferred is an analytical system for the determination of one or more analytes, comprising
an arrangement according to any of the aforementioned embodiments means for the locally addressed supply of samples or reagents to the sample compartments of the arrangement at least one excitation light source, and at least one detector for the detection of a change of an optical parameter (measurand), which is preferably a change of the refractive index and/or of one or more luminescences in the vicinity of the one or more analytes.

A characteristic of a possible embodiment of the analytical system is that the launching of the excitation light to the measurement areas (d) is performed in a surface or transmissive illumination configuration.

For specific applications, it is of advantage if the launching of the excitation light to the measurement areas (d) and the detection of the measurement light from the measurement areas (d) is performed at opposite sides of the base plate.

For a larger number of applications, it is preferred that the launching of the excitation light to the measurement areas (d) and the detection of the measurement light from the measurement areas (d) is performed at the same side of the base plate.

A characteristic of a special embodiment is that the launching of the excitation light to the measurement areas (d) and the detection of the measurement light from the measurement areas (d) is performed in a confocal arrangement.

For another embodiment of the analytical system according to the invention, with an arrangement of sample compartments according to the invention, comprising an optical film waveguide, it is preferred that the excitation light rays of one (common) wavelength are located in a common plane, which is defined by the resonance angle for in-coupling the excitation light of the excitation wavelength into the optically transparent layer (a) by an optical coupling element.

For the simultaneous detection of signals from a multitude of measurement areas, it is preferred that at least one laterally resolving detector is used for signal detection, which is preferably selected from the group formed by CCD cameras, CCD chips, photodiode arrays, Avalanche diode arrays, multi-channel plates, and multi-channel photomultipliers.

The invention encompasses analytical systems, the characteristics of which is that optical components of the group comprising lenses or lens systems for the shaping of the transmitted light bundles, planar or curved mirrors for the deviation and optionally additional shaping of the light bundles, prisms for the deviation and optionally spectral separation of the light bundles, dichroic mirrors for the spectrally selective deviation of parts of the light bundles, neutral density filters for the regulation of the transmitted light intensity, optical filters or monochromators for the spectrally selective transmission of parts of the light bundles, or polarization selective elements for the selection of discrete polarization directions of the excitation or luminescence light are located between the one or more excitation light sources and the base plate, as part of an arrangement according to any of the aforementioned embodiments, and/or between the base plate and the one or more detectors.

The light excitation can be performed continuously. It is preferred, however, that the excitation light is launched in pulses with duration of 1 fsec to 10 min.

A characteristic of an advanced embodiment of the analytical system is that the emission light from the measurement areas is measured time-resolved.

It is preferred that for referencing the available excitation light, light signals of the group comprising excitation light at the location of the light sources or after expansion of the excitation light or after its multiplexing into individual beams, scattered light at the excitation wavelength from the location of the one or more discrete measurement areas, and light of the excitation wavelength outcoupled by the grating structures (c) or (c') are measured.

It is especially preferred that the measurement areas for determination of the emission light and of the reference signal are identical.

In one embodiment of the analytical system according to the invention, launching and detection of the emission light is performed simultaneously for all measurement areas. A characteristic of another embodiment is that launching of the excitation light and detection of the emission light from the one or more measurement areas is performed sequentially for one or more sample compartments. It is also possible that sequential launching of the excitation light and detection of the emission light from one or more measurement areas is performed several times within a single sample compartment.

Thereby, it is preferred that sequential excitation and detection is performed using movable optical components of the group comprising mirrors, deviating prisms, and dichroic mirrors.

It is preferred, that sequential excitation and detection is performed using an essentially focus and angle preserving scanner.

A characteristic of another embodiment of an analytical system with sequential excitation and detection is that the arrangement, according to any of the aforementioned embodiments, is moved between steps of sequential excitation and detection.

A further subject of the invention is a method for manufacturing an arrangement of sample compartments in a one- or two-dimensional array, comprising a base plate and a body combined with the base plate in such a way that an array of (spatial) recesses for generation of an array of flow cells, each with at least one inlet and one outlet, are formed between the base plate and the body, wherein at least one outlet of each flow cell is joined with a reservoir fluidically connected with the flow cell, the reservoir being operable to receive liquid exiting the flow cell, wherein the base plate and the body are combined in such a way that different ones of the (spatial) recesses are fluidically sealed against one another.

As a possible embodiment of this method, the base plate and the body combined with the base plate can be joined irreversibly. Thereby, it is preferred that the base plate and the body combined with the base plate are glued together.

Thereby, a glue is preferred which is characterized by transparency as high as possible, at least at the excitation wavelength, and is fluorescent as weak as possible under the excitation conditions, in the ideal case free of fluorescence. For applications, wherein the excitation light shall be restricted to a single sample compartment, however, it can also be advantageous if the glue is absorbent at the excitation wavelength, for example black, but again fluorescent as low as possible, in the ideal case free of fluorescence. Furtheron, similar material requirements hold for the glue as for the material of the body combined with the base plate, i.e. chemical and physical stability, for example upon exposure to acidic or basic media, salts, alcohols, or detergents as parts of aqueous solutions, or formamide, and temperature stability. Of course, the glue has to be adapted simultaneously to the chemical surface properties of the materials to be joined. Chemical reactions with analytes and/or the immobilized recognition elements shall also not occur.

If the biological or biochemical or synthetic recognition elements for the analyte determination are deposited on the base plate before the combination with the body, the compatibility of the necessary glue curing method with the stability of the recognition elements also has to be taken into account. This, in general, excludes those glues, which require for curing the application of very short-wavelength UV-radiation (e.g. shorter than 280 nm), of high temperatures (e.g. above 100° C.), especially when required for longer periods (e.g. longer than 2 hours). Thereby, the requirements are generally stricter, when proteins, such as antibodies, are used as recognition elements, than in combination with nucleic acids as recognition elements.

The base plate and the body combined therewith can also be joined reversibly, for example by latching, enabled by adequate means provided to that body, such as barbed hooks, or by inserting into provided guideways. An essential criterium for the choice of the method for the joining of the base plate with the body is, that after its accomplishment, adjacent sample compartments are fluidically sealed against one another. The fluidic sealing can optionally be supported by using formable sealing materials. For example, the body can be provided as two- or more-component (layer) system, the layer facing the base plate being formed by an elastic material, or gaskets ("O-rings") can be used for sealing. Also the application of a diffusion barrier, in form of a recess in the separation wall between adjacent sample compartments, the separation wall being brought into contact with the base plate, can be intended for this purpose.

Part of the invention is a method for the determination of one or more analytes in one or more liquid samples with an arrangement according to any of the aforementioned embodiments and an analytical system according to any of the aforementioned embodiments, wherein sample and optionally additional reagent solutions are supplied to the sample compartments, and wherein these liquids can exit into a reservoir fluidically connected with the flow cell, as part of the sample compartments.

A characteristic of an advanced embodiment of the method is that biological or biochemical or synthetic recognition elements for the determination of one or more analytes are immobilized on the base plate of the arrangement, excitation light is directed to the measurement areas on the base plate, and the light emanating from the measurement areas is detected by at least one detector.

Thereby, a method is preferred wherein the base plate comprises an optical waveguide, which is continuous or partitioned into discrete areas, excitation light is launched into the waveguide using an optical coupling element, and measurement light from the measurement areas, which are in optical interaction with the optical waveguide, is detected by one or more detectors.

Especially preferred is a method, wherein the optical waveguide is provided as an optical film waveguide, with a first optically transparent layer (a) on a second optically transparent layer (b) with lower refractive index than layer (a), wherein furthermore excitation light is in-coupled into the optically transparent layer (a), by one or more grating structures formed in the optically transparent layer (a), and directed, as a guided wave, to the measurement areas located thereon, and wherein furthermore the luminescence from molecules capable to luminesce, which is generated in the evanescent field of the guided wave, is detected by one or more detectors, and wherein the concentration of one or more analytes is determined from the intensity of these luminescence signals.

In case of arrangements with grating structures (c) for the in-coupling of excitation light and additionally provided grating structures (c') for the out-coupling of light guided in the waveguiding layer, the in-coupling can be optimized by directing the excitation light out-coupled by a grating structure (c'), directly or after ray deviation, by means of mirrors or prisms, and optionally after focusing by means of an adequate lens, onto a detector, such as a photodiode connected to an amplifier. Thereby, it is preferred that the excitation light is out-coupled along the whole width (dimension normal to the direction of propagation of the guided excitation light in the plane of the waveguiding layer) and is focused onto the light-sensitive area of the detector. An optimum in-coupling is achieved when the signal of the out-coupled light generated by this detector reaches its maximum.

It is especially preferred that (1) the isotropically emitted luminescence or (2) luminescence that is in-coupled into the optically transparent layer (a) and out-coupled by a grating structure (c) or luminescence comprising both parts (1) and (2) is measured simultaneously.

Part of the method according to the invention is that for the generation of the luminescence, a luminescent dye or a luminescent nano-particle is used as a luminescence label, which can be excited and emits at a wavelength between 300 nm and 1100 nm.

It is preferred that the luminescence label is bound to the analyte or, in a competitive assay, to an analyte analogue or, in a multi-step assay, to one of the binding partners of the immobilized biological or biochemical or synthetic recognition elements or to the biological or biochemical or synthetic recognition elements.

A characteristic of another embodiment of the method is that a second or more luminescence labels of similar or different excitation wavelength as the first luminescence label and similar or different emission wavelength are used.

Thereby, it is preferred that the second or more luminescence labels can be excited at the same wavelength as the first luminescence label, but emit at other wavelengths.

It is especially advantageous if the excitation and emission spectra of the applied luminescent dyes do not overlap or overlap only partially.

A characteristic of another embodiment of the method is that charge or optical energy transfer from a first luminescent dye, acting as a donor, to a second luminescent dye, acting as an acceptor, is used for the detection of the analyte.

A characteristic of still another embodiment of the method is that besides determination of one or more luminescences, changes of the effective refractive index on the measurement areas are determined.

In an advanced embodiment of the method, the one or more determinations of luminescences and/or determinations of light signals at the excitation wavelength are performed polarization-selective.

It is preferred that the one or more luminescences are measured at a polarization that is different from the one of the excitation light.

Part of the invention is a method according to any of the aforementioned embodiments for the simultaneous or sequential, quantitative or qualitative determination of one or more analytes of the group comprising antibodies or antigens, receptors or ligands, chelators or "histidin-tag components", oligonucleotides, DNA or RNA strands, DNA or RNA analogues, enzymes, enzyme cofactors or inhibitors, lectins and carbohydrates.

A characteristic of possible embodiments of the method is that the samples to be examined are naturally occurring body fluids, such as blood, serum, plasma, lymphe or urine or tissue fluids, or egg yolk.

A characteristic of other embodiments is that the samples to be examined are optically turbid liquids or surface water or soil or plant extracts or bio- or process broths.

The samples to be examined can also be taken from biological tissue.

A further subject of the invention is the use of a method according to any of the aforementioned embodiments for the quantitative or qualitative determination of chemical, biochemical or biological analytes in screening methods in pharmaceutical research, combinatorial chemistry, clinical and preclinical development, for real-time binding studies and the determination of kinetic parameters in affinity screening and in research, for qualitative and quantitative analyte determinations, especially for DNA- and RNA analytics and for the determination of genomic or proteomic differences in the genome, such as single nucleotide polymorphisms, for the measurement of protein-DNA interactions, for the determination of control mechanisms for mRNA expression and for the protein (bio)synthesis, for the generation of toxicity studies and the determination of expression profiles, especially for the determination of biological and chemical marker compounds, such as mRNA, proteins, peptides or small-molecular organic (messenger) compounds, and for the determination of antibodies, antigens, pathogens or bacteria in pharmaceutical product development and research, human and veterinary diagnostics, agrochemical product development and research, for symptomatic and pre-symptomatic plant diagnostics, for patient stratification in pharmaceutical product development and for the therapeutic drug selection, for the determination of pathogens, nocuous agents and germs, especially of salmonella, prions and bacteria, in food and environmental analytics.

EXAMPLES

The arrangement according to the invention is exemplified in the following figures, without restriction of the subject of the invention.

Example 1

It is of advantage if the arrangements of sample compartments according to the invention are stackable, and if they comprise means for avoiding a contamination of the base plates 4, upon contact with the environment.

Figure 1:
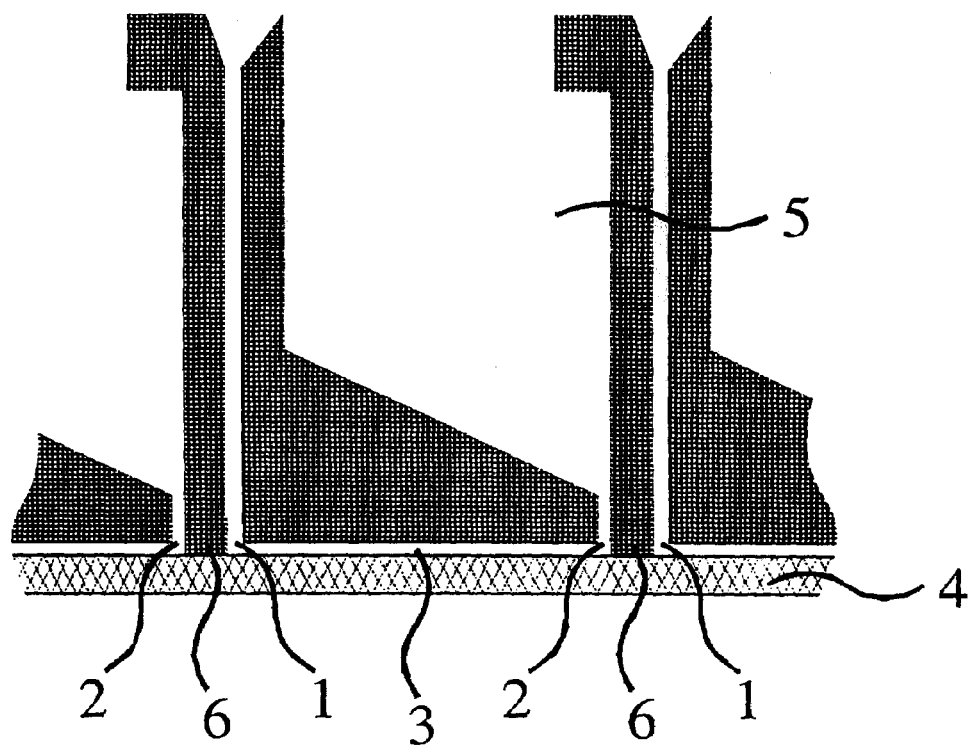
FIG. 1 shows a cross-sectional partial view, comprising the inlet and outlet of a single flow cell and parts of the adjacent flow cell.

The arrangement according to FIG. 1 comprises a base plate 4 and a body 6 combined therewith. The body has a recess 3, which forms a spatial (three-dimensional) recess for generation of a flow cell, with an inlet 1 and an outlet 2, after combination of the body with the base plate. The recess 3 can have any geometrical base area; for example, it can be rectangular. It is preferred that the corners are rounded (not shown in the figures). The diameters and cross-sectional areas of inlets 1 and outlets 2 can be identical or different, and can remain constant or changing between the inlet opening for the liquid addition and the entrance into the three-dimensional recess 3, respectively between the exit from the spatial (three-dimensional) recess 3 and the entrance into the reservoir 5 fluidically connected to this flow cell.

For a reduction of sample and reagent volumes required for filling the flow cells, it can be advantageous if the inlet section 1 is broadened in such a way, that also pipet tips of larger diameter can be inserted into the inlet, and if the inlet section is closed again at its lower end, except for a narrow opening for the entrance into the recess 3. The later entrance opening can additionally be surrounded by a low surrounding wall, within the inlet section 1 (not shown). An additional sealing of the inlet 1 against adjacent reservoirs 5 can be achieved, for example, if a conically shaped (tapered) pipet tip of a soft, elastic material is pressed against a harder wall material of the body 6 (especially concerning the walls of the inlet 1), thus providing a sealing function.

For enabling the use of larger pipet tips for the filling step, it can be further advantageous, if the pitch (geometrical arrangement in rows and columns) of the reservoirs 5 is displaced with respect to the pitch of the flow cells, including their recesses 3 and the related inlet openings of the inlets 1, in such a way that the entrance openings are always located at the edge or at a corner of a recess 3 (as shown in FIG. 1), but that the walls (as part of the body 6) towards the reservoir 5 are displaced in direction towards the next flow cell. This configuration can be helpful for avoiding, within the recesses 3, dead volumes without flow, and for simultaneously keeping low the required liquid volumes.

For facilitating the filling step, the inlet 1 can, for example, be shaped conically (tapered), such that a tip inserted into this inlet is guided towards the entrance opening of the recess 3. The insertion can further be facilitated by additional, mechanically structured aids, such as grooves or ripples in a (conical) entrance opening, towards said entrance opening in direction of the recess 3 Further, concentrical ring structures in the wall of the inlet can be provided as aids for centering.

Further, the addition of components, such as detergents, reducing the surface tension of the supplied liquids and thus reducing the contact angle with the walls of the flow cells, to the supplied sample and to reagent solutions can facilitate the filling process and avoid the formation of air bubbles during the filling step. For the same purpose, it can be helpful if the walls of the body 6 are themselves modified by chemical or physical surface treatment, such as plasma treatment, in such a way, that the contact angle is reduced and the wettability thus improved.

Also shown is the inlet 2 respectively the outlet 1 of the adjacent flow cells (in this cross-sectional view). It is preferred that the inlet and the outlet of a flow cell are always located at opposite corner points of the base area of the recess, in case of an essentially rectangular base area for example at the endpoints of the diagonal.

In order to allow for a more constant filling and fill velocity respectively surface wetting of the base plate 4 (for avoiding a parabolic flow profile in the cross-sectional plane normal to FIG. 1), it can be of advantage if the recesses 3 have an increased depth in direction normal to the figure plane, i.e. if the flow cross section is not rectangular or elliptic, but expanded towards the edges. Thus, a more even flow velocity within the cross-sectional distribution can be achieved, and the formation of dead volumes in the border regions can again be reduced.

Example 2

Figure 2:
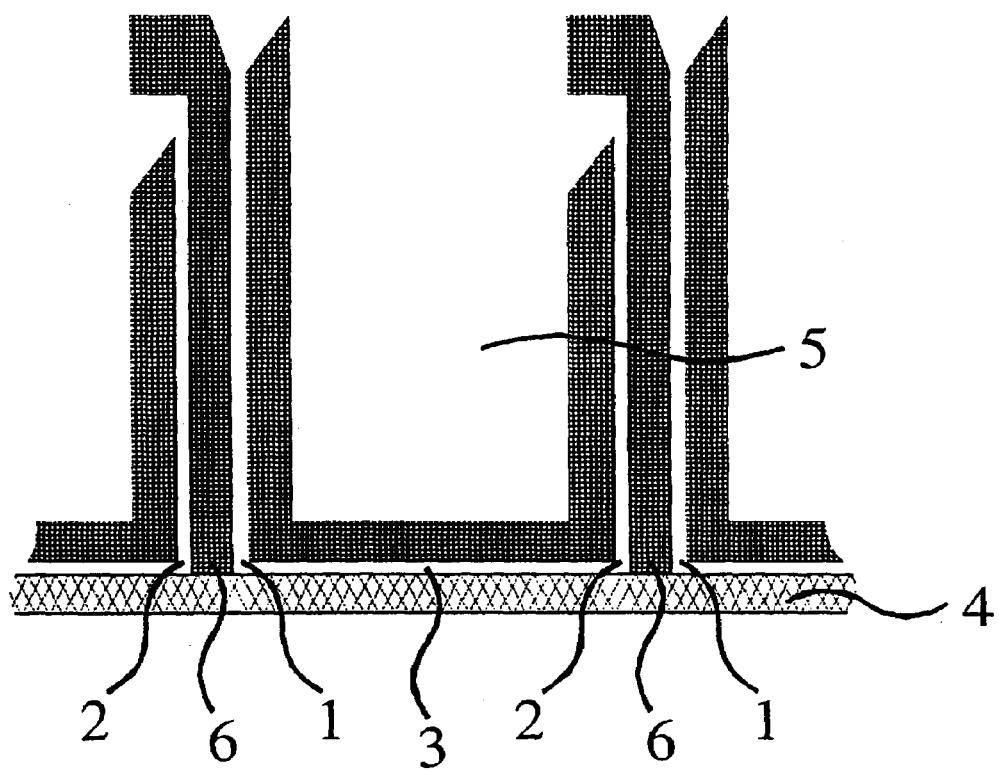
FIG. 2 shows a cross-sectional partial view corresponding to FIG. 1, for another embodiment of the arrangement according to the invention.

FIG. 2 shows another embodiment of the arrangement according to the invention, wherein the reservoir 5 is provided as a recess in the exterior wall of the body combined with the base plate 4. In this embodiment, liquid exiting the flow cell can enter the reservoir 5, but cannot flow back into the flow cell, as long as the reservoir is not filled up to the upper edge of the side wall at the site of the liquid exit.

Example 3

Figure 3:
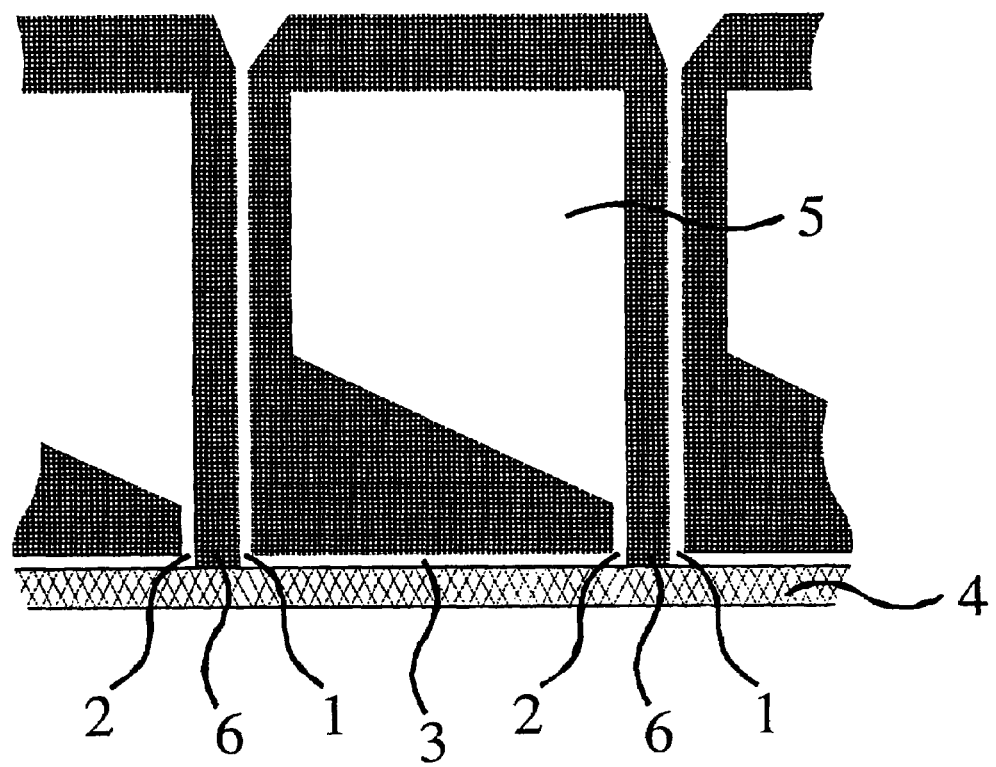
FIG. 3 depicts shows a cross-sectional partial view corresponding to FIG. 1, for still another embodiment of the arrangement according to the invention.

FIG. 3 shows a modified version of an arrangement according to FIG. 1, wherein the reservoir 5 is closed on top. As a consequence, liquid cannot escape, by evaporation, from the reservoir as well. This variant is associated with the additional advantage that such an arrangement according to the invention can be fluidically sealed completely, especially safe, upon using an additional covering top, such as a foil, a septum or a cover plate. This is of special importance and advantageous, if, for example, an escape of biologically or chemically hazardous molecules or liquids from the arrangement according to the invention shall be prevented after the use.

With respect to all described examples, the body 6 can consist of a single or also of several pieces, which are preferably combined to a unit irreversibly.

Example 4

Figure 4:
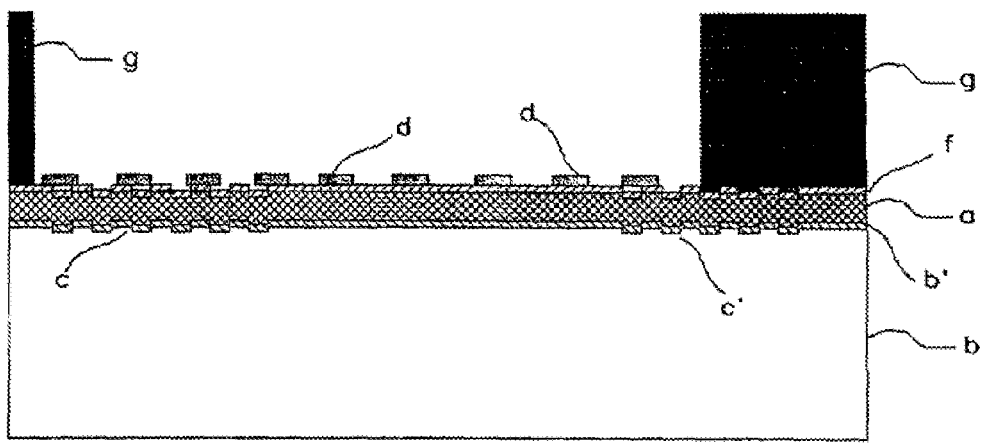
FIG. 4 depicts a cross-sectional partial view, restricted to the base plate, for an embodiment with an optical film waveguide as the base plate.

FIG. 4 exemplifies an arrangement according to the invention, wherein the base plate is provided as an optical film waveguide with biological or biochemical recognition elements immobilized thereon. Here, with "g" are denoted the bordering walls of a flow cell, which is generated upon combination of the base plate with a body 6, according to the examples described before. Therefore, "g" corresponds to the denoting label "6" in FIGS. 1-3.

On a layer (b), which is transparent at least in a part of the visible or near-infrared spectral region, first a thin intermediate layer (b') and then a layer (a) is deposited, the refractive index of which is larger than the refractive indices of layers (b) and (b'). The layers (a) and (b') are also optically transparent at least in a part of the visible and near-infrared spectral range. Grating structures (c) and (c') are provided in form of relief gratings in layer (b), which gratings are transferred into the layers located above upon their deposition. Then an adhesion-promoting layer (f) is deposited on layer (a), which can improve the adhesion of biological or biochemical or synthetic recognition elements to be immobilized. In the provided example, the recognition elements are immobilized in discrete (laterally separated) measurement areas (d), which can be arranged, according to this embodiment, both on and between the grating structures (c) and (c'). In this example, the base plate is finally combined with the body (g) (corresponding to "6" according to the denotation for FIGS. 1-3).

Example 5

Figure 5:
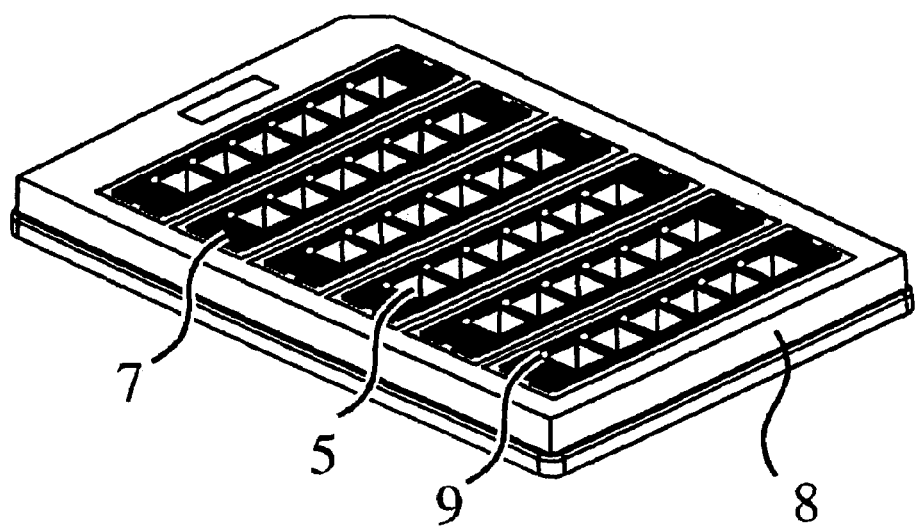
FIG. 5 shows an arrangement, wherein column-like arrangements of base plates and the bodies combined therewith (according to the arrangement of FIG. 2), for generation of, for example, 6 columns with 6 flow cells each, are themselves then inserted into a common carrier ("meta-carrier").

FIG. 5 shows an arrangement, wherein column-like arrangements of base plates and the bodies combined therewith (according to the arrangement of Example 2), for generation of six total columns with six flow cells each, are themselves then inserted into a common carrier ("meta-carrier"). The column-like base plates 4 and bodies 6 combined therewith together form insertion modules 7, which are inserted into the meta-carrier 8.

In the shown example, the meta-carrier has the foot print of a microtiter plate. The inlet openings 9 towards the inlets 1 (not shown in this figure) are positioned in such a way, that they are compatible with the pitch (geometrical arrangements in rows and columns) of a 96-well standard microtiter plate, i.e., they are always positioned at intervals of a whole-numbered multiple of 9 mm (in this example: interval of the inlets within a column: 9 mm; interval of the inlets between adjacent columns: 18 mm). Upon an adequate displacement of the meta-carrier, together with the insertion modules, the geometrical arrangement of the reservoirs 5 is compatible with the pitch of a standard 96-well microtiter plate correspondingly.

In the shown example, the meta-carrier is provided in such an embodiment that it can receive up to six insertion modules. However, sites for insertion modules can also remain vacant.

The insertion of the insertion modules into the meta-carrier, optionally also in an automated way, can be facilitated by mechanical aids, such as mechanical limit points or walls, aids for centering, such as mechanical guides or optical marks.

The adjoining of the arrangement of sample compartments with the meta-carrier can, for example, be performed by glueing or by exact fitting without glueing, if it is intended for single-use, or, for example by latching or inserting into an adequately formed mounting, if it is intended for multiple use.

The shown example illustrates an embodiment of a reusable meta-carrier, into which the insertion modules 7 are introduced by means of an attachment mechanism and from where they can be removed again, after execution of a measurement.

Preferably, the insertion modules 7 with rows or columns of flow cells and the corresponding receiving sites of the meta-carrier are provided in such a form that only a single orientation of the insertion modules is possible upon their insertion.

The invention claimed is:

1. An arrangement of sample compartments in a one-dimensional or a two-dimensional array, said arrangement comprising:
    a base plate; and
    a body combined with said base plate so as to form an array of recesses between said base plate and said body,
    wherein said array of recesses generates an array of flow cells fluidically sealed against one another,
    wherein each of said flow cells includes at least one inlet and at least one outlet,
    wherein, for each of said flow cells, said at least one outlet is joined with a reservoir fluidically connected with said flow cell, said reservoir being operable to receive liquid exiting from said at least one outlet of said flow cell, wherein a fluid uptake capacity of said reservoir is equal to or higher than a fluid uptake capacity of said recess forming said flow cell, and wherein said reservoir is formed as a recess in said body.

2. An arrangement according to claim 1, wherein three-dimensional structures with a geometrical arrangement in rows and/or columns of the arrays of flow cells to be generated, are formed on said base plate.

3. An arrangement according to claim 1, wherein, for generation of the array of recesses between said base plate and said body combined therewith, recesses are formed in said base plate.

4. An arrangement according to claim 1, wherein, for generation of the array of recesses between said base plate and said body combined therewith, recesses are formed in said body.

5. An arrangement according to claim 1, wherein said body is made of several parts which form an irreversibly combined unit.

6. An arrangement according to claim 1, wherein said arrangement comprises 2-2000 flow cells.

7. An arrangement according to claim 1, wherein a geometrical arrangement in rows and/or columns of the inlets of said flow cells corresponds to a geometrical arrangement of wells of a standard microtiter plate.

8. An arrangement according to claim 1, with 2 to 8 of said sample compartments in a column or 2 to 12 of said sample compartments in a row, wherein said sample compartments are combined with a meta carrier, said meta carrier having dimensions of a standard microtiter plate such a geometrical arrangement in rows and/or columns of said inlets of said flow cells corresponds to a geometrical arrangement of wells of a standard microtiter plate.

9. An arrangement according to claim 1, wherein said arrangement of sample compartments is closed by a covering top.

10. An arrangement according to claim 1, wherein an inner volume of each flow cell is 0.1 µl-1000 µl.

11. An arrangement according to claim 1, wherein a capacity of said reservoir fluidically connected to said flow cell is at least 5 times larger than an inner volume of said flow cell.

12. An arrangement according to claim 1, wherein a depth of said recesses between said base plate and said body combined with said base plate is 1-1000 µm.

13. An arrangement according to claim 1,
wherein base areas of the recesses between said base plate and said body combined with said base plate are 0.1 $mm^2$-200 $mm^2$ each,
wherein the size of said recesses of an array is uniform or diverse, and wherein the base areas of said recesses are rectangular or polygonal.

14. An arrangement according to claim 9, wherein materials of said base plate, of said body combined with said base plate, and of said covering top are selected from formable, moldable or millable plastics, metals, silicates, or ceramics.

15. An arrangement according to claim 1, wherein biological or biochemical or synthetic recognition elements for the determination of one or more analytes are immobilized on said base plate.

16. An arrangement according to claim 1, wherein an adhesion-promoting layer is deposited on said base plate for immobilization of biological or biochemical or synthetic recognition elements.

17. An arrangement according to claim 16, wherein said adhesion-promoting layer has a thickness of less than 200 nm.

18. An arrangement according to claim 16, wherein said adhesion-promoting layer comprises chemical compounds from the groups of silanes, epoxides, self-organized functionalized monolayers, functionalized polymers and polymer gels.

19. An arrangement according to claim 1,
wherein biological or biochemical or synthetic recognition elements are immobilized in discrete measurement areas, and
wherein said discrete measurement areas are formed by spatially selective deposition of biological or biochemical or synthetic recognition elements on said base plate.

20. An arrangement according to claim 19, wherein the biological or biochemical or synthetic recognition elements are deposited on said base plate by one or more methods selected from ink jet spotting, mechanical spotting by means of pin, pen or capillary, micro contact printing, fluidically contacting the measurement areas with the biological or biochemical or synthetic recognition elements upon their supply in parallel or crossed micro channels, upon exposure to pressure differences or to electric or electromagnetic potentials.

21. An arrangement according to claim 19, wherein, as said biological or biochemical or synthetic recognition elements, components from the groups formed by nucleic acids (DNA, RNA) or nucleic acid analogues, antibodies, aptamers, membrane-bound and isolated receptors, their ligands, antigens for antibodies, cavities generated by chemical synthesis to host molecular imprints, and histidin-tag components, are deposited.

22. An arrangement according to claim 19, wherein, as said biological or biochemical or synthetic recognition elements, whole cells or cell fragments are deposited.

23. An arrangement according to claim 1, wherein arrays of two or more discrete measurement areas each are arranged in regions of said recesses between said base plate and said body combined with said base plate, in which measurement areas having similar or different biological or biochemical or synthetic recognition elements are immobilized.

24. An arrangement according to claim 19, wherein compounds which are chemically neutral toward an analyte are deposited between said discrete measurement areas.

25. An arrangement according to claim 24, wherein said chemically neutral compounds are selected from albumins, herring sparm or polyethylen glycols.

26. An arrangement according to claim 1, wherein said base plate with biological or biochemical or synthetic recognition elements immobilized thereon is operable for the determination of a change of optical, electrical, electrochemical or thermal parameters, or for the determination of radioactive radiation.

27. An arrangement according to claim 26,
wherein said base plate with the biological or biochemical or synthetic recognition elements immobilized thereon is operable for the determination of a change of optical parameters, and
wherein said base plate is transparent in at least one region of wavelengths in the visible or near-infrared spectral region.

28. An arrangement according to claim 1,
wherein said base plate comprises a supporting substrate of glass or of a thermoplastic or moldable plastic, and
wherein said base plate is transparent in at least one region of wavelengths in the visible or near-infrared spectral region.

29. An arrangement according to claim 1, wherein said base plate comprises an optical waveguide, said optical waveguide being continuous or partitioned into discrete areas.

30. An arrangement according to claim 29, wherein said optical waveguide is an optical film waveguide with a first optically transparent layer, facing the recesses, on a second optically transparent layer with lower refractive index than said first optically transparent layer.

31. An arrangement according to claim 30, wherein a material of the second optically transparent layer comprises silicates or a transparent thermoplastic or moldable plastic selected from polycarbonate, polyimide, polymethylmethacrylate, or polystyrene.

32. An arrangement according to claim 30, wherein a refractive index of said first optically transparent layer is higher than 1.8.

33. An arrangement according to claim 30, wherein said first optically transparent layer comprises $TiO_2$, $ZnO$, $Nb_2O_5$, $Ta_2O_5$, $HfO_2$, or $ZrO_2$.

34. An arrangement according to claim 30, wherein a thickness of said first optically transparent layer is between 40 and 300 nm.

35. An arrangement according to claim 30, wherein an additional optically transparent layer with a lower refractive index than said first optically transparent layer, and in contact with said first optically transparent layer, and with a thickness of 5 nm-10,000 nm is located between said first and second optically transparent layers.

36. An arrangement according to claim 30, wherein in-coupling of excitation light into said first optically transparent layer and to said measurement areas is performed using one or more optical in-coupling elements selected from prism couplers, evanescent couplers comprising joined optical waveguides with overlapping evanescent fields, front face couplers with focusing lenses arranged in front of a front face of a waveguiding layer, and grating couplers.

37. An arrangement according to claim 30, further comprising one or more grating structures formed in said first optically transparent layer,
wherein in-coupling of excitation light into said first optically transparent layer and to said measurement areas is performed using said one or more grating structures.

38. An arrangement according to claim 30, wherein out-coupling of light guided in said first optically transparent layer is performed using said one or more grating structures that are formed in said first optically transparent layer.

39. An arrangement according to claim 37,
wherein out-coupling of light guided in said first optically transparent layer is performed using said one or more grating structures that are formed in said first optically transparent layer
wherein said one or more grating structures comprises a plurality of grating structures, and
wherein said grating structures formed in said first optically transparent layer have the same or different periodicity and are arranged in parallel or not in parallel to one another.

40. An arrangement according to claim 39, wherein said grating structures can interchangeably be used as in-coupling and/or out-coupling gratings.

41. An arrangement according to claim 37, wherein said one or more grating structures comprises a plurality of grating structure, and
wherein said grating structures have a period of 200 nm-1000 nm and a grating modulation depth of 3 nm-100 nm.

42. An arrangement according to claim 41, wherein a ratio of a modulation depth to a thickness of said first optically transparent layer is equal or smaller than 0.2.

43. An arrangement according to claim 37, wherein said one or more grating structures is a relief grating or a phase or volume grating with a periodic modulation of refractive index in said first optically transparent layer.

44. An arrangement according to claim 30,
wherein a thin metal layer disposed on an additional dielectric layer of lower refractive index than said first optically transparent layer is deposited between said first optically transparent layer and immobilized biological or biochemical recognition elements, and
wherein a thickness of said metal layer and said additional intermediate layer is selected such that a surface plasmon at an excitation wavelength and/or at a luminescence wavelength can be excited.

45. An arrangement according to claim 37, wherein said one or more grating structures is a diffractive grating with a uniform period.

46. An arrangement according to claim 37, wherein said one or more grating structures is a multi-diffractive grating.

47. An arrangement according to claim 37, wherein said one or more grating structures are located within a region of said sample compartments.

48. An arrangement according to claim 37, wherein said one or more grating structures are located outside a region of said sample compartments.

49. An arrangement according to claim 37, wherein said one or more grating structures extend over a range of multiple or all of said sample compartments.

50. An arrangement according to claim 37,
wherein said one or more grating structures comprises a plurality of grating structures,
wherein at least one of said grating structures is located within a region of said sample compartments, and
wherein at least one of said grating structures is located outside of said sample compartment, within which the in-coupling of excitation light is performed.

51. An arrangement according to claim 1, wherein a material of said body combined with said base plate, in an incumbant surface area on said base plate, is optically transparent, both for excitation radiation and for one or more optionally excited luminescence radiations, at least within a penetration depth of an evanescent field.

52. An arrangement according to claim 51, wherein a material of said body combined with the base plate is provided in a form of a two-layer system, the first layer of which, to be brought into contact with a surface of said base plate, being transparent both for the excitation radiation and for one or more optionally excited luminescence radiations, whereas an adjacent layer, being located more remote from said base plate is absorbent in a spectral range of the excitation radiation and of the optionally excited luminescence radiations.

53. An arrangement according to claim 47, wherein a material of a layer in contact with said base plate is absorbent in a spectral range of an excitation radiation and of optionally excited luminescence radiations.

54. An arrangement according to claim 1, wherein a material of a layer of said body in contact with said base plate is self-adhesive and tightly sealing.

55. An arrangement according to claim 1, wherein a material of a layer of said body in contact with the base plate comprises a polysiloxane.

56. An arrangement according to claim 1, wherein 5-1000 measurement areas are located in one sample compartment.

57. An arrangement according to claim 1, wherein optically or mechanically recognizable marks are provided on said base plate in order to facilitate adjustment in an optical system and/or to facilitate the combination of said base plate with said body comprising said recesses for said sample compartments.

* * * * *